United States Patent
Dilger

[19]
[11] Patent Number: 6,029,506
[45] Date of Patent: Feb. 29, 2000

[54] SAMPLE RETRIEVAL SYSTEM

[75] Inventor: John P. Dilger, Marshalltown, Iowa

[73] Assignee: Fisher Controls International, Inc., Marshalltown, Iowa

[21] Appl. No.: 08/968,545

[22] Filed: Nov. 12, 1997

[51] Int. Cl.[7] .................................................. G01N 1/24
[52] U.S. Cl. ................................................................. 73/46
[58] Field of Search ........................ 73/40.7, 46, 863.83, 73/864.34, 864.73

[56] References Cited

U.S. PATENT DOCUMENTS

| | | |
|---|---|---|
| 3,950,136 | 4/1976 | Bellinga et al. . |
| 4,138,381 | 2/1979 | Graves et al. ........................... 73/421.5 |
| 4,226,113 | 10/1980 | Pelletier et al. ........................... 73/40.7 |
| 4,441,356 | 4/1984 | Bohl ............................................. 73/23 |
| 4,674,343 | 6/1987 | Larson et al. . |
| 4,901,751 | 2/1990 | Story et al. .................................. 73/46 |
| 4,972,867 | 11/1990 | Ruesch ........................................ 73/46 |
| 5,056,355 | 10/1991 | Hepher et al. ........................... 73/24.03 |
| 5,297,432 | 3/1994 | Traina et al. . |
| 5,417,105 | 5/1995 | Martinez et al. ..................... 73/864.73 |
| 5,469,731 | 11/1995 | Decker et al. .......................... 73/23.31 |
| 5,544,208 | 8/1996 | Pao et al. . |

FOREIGN PATENT DOCUMENTS

| | | | |
|---|---|---|---|
| 0 344 618 A2 | 12/1989 | European Pat. Off. ......... | G01N 1/22 |
| 0 344 618 A3 | 12/1989 | European Pat. Off. ......... | G01N 1/22 |
| 0 503 841 A2 | 9/1992 | European Pat. Off. ......... | G01N 1/26 |
| 0 710 829 A1 | 11/1994 | European Pat. Off. ......... | G01N 1/24 |

OTHER PUBLICATIONS

*Control Engineering*, "Controlling Fugitive Emissions In Control Valves", Jacques Chemoul, pp. 107, 108, 110, and 112, Sep. 1995.

*Control Engineering*, "Valve Users Get Help On Fugitive Emissions", George J. Blickley, pp. 117, 118, 120 and 122, Sept. 1995.

*Journal of Applied Mechanics*, "A Simple Air Ejector", J. H. Keenan, et al, pp. A–75–A81, Jun. 1942.

*Primary Examiner*—Robert Raevis
*Attorney, Agent, or Firm*—Arnold White & Durkee

[57] ABSTRACT

A method and apparatus for collecting fugitive emissions from valves and other emissions sources is disclosed. The apparatus comprises a capsule enclosing at least a portion of the equipment and an ejector in fluid flow communication with the capsule. The ejector is connected to a compressed air source, which creates a pressure drop in the ejector which draws emissions from the capsule into the ejector. The apparatus may include a sensor chamber housing gas sensors to detect the presence and concentration of any emissions from the equipment being monitored, and may store emissions data, communicate the data to a plant process control system, and use the data to control plant conditions to reduce or eliminate the emissions.

16 Claims, 4 Drawing Sheets

SAMPLE RETRIEVAL SYSTEM

BACKGROUND OF THE INVENTION

A. Field of the Invention

The present invention relates generally to systems for collecting fluid samples and, more particularly, to an apparatus and method for collecting fugitive emissions from process equipment.

B. Description of the Related Art

Industrial plants that handle volatile organic compounds (VOCs) typically experience unwanted emissions of those compounds into the atmosphere from point sources such as smokestacks and non-point sources such as valves, pumps, and fittings installed on pipes and vessels containing the VOCs. Emissions from non-point sources, referred to as "fugitive" emissions, typically occur due to leakage of the VOCs from joints and seals. Fugitive emissions from control valves may occur as leakage through the packing between the valve stem and body of the valve. Valves employed in demanding service conditions involving frequent movement of the valve stem and large temperature fluctuations typically suffer accelerated deterioration of the valve stem packing, resulting in greater fugitive emissions than valves in less demanding service.

While improvements in valve stem packing materials and designs have reduced fugitive emissions and lengthened the life of valve packing, the monitoring of fugitive emissions has become important as a means to identify and reduce fugitive emissions and comply with new more stringent regulation of emissions. The Environmental Protection Agency (EPA) has promulgated regulations specifying the maximum permitted leakage of certain hazardous air pollutants from control valves, and requiring periodic surveys of emissions from control valves.

Current methods of monitoring fugitive emissions involve manual procedures using a portable organic vapor analyzer. This manual method is time consuming and expensive to perform, and can also yield inaccurate results due to ineffective collection of the fugitive emissions from the equipment being monitored. If measurements are made on a valve exposed to wind, emissions from the valve may be dissipated before the vapor analyzer can properly measure the concentration of the emissions. Also, if the analyzer is not carefully moved around the valve to capture all the emissions from the valve, an inaccurate measurement will result. Manual measurement methods also require plant personnel to dedicate a significant amount of time to making the measurements, distracting from their other duties.

Automated monitoring and detection of fugitive emissions can yield significant advantages over existing manual methods. The EPA regulations require surveys of fugitive emissions at periodic intervals. The length of the survey interval may be monthly, quarterly, semi-annual, or annual; the required surveys becoming less frequent if the facility operator can document fewer than a certain percentage of control valves with excessive leakage. Thus, achieving a low percentage of leaking valves reduces the number of surveys required per year. In a large industrial facility where the total number of survey points can range from 50,000 to 200,000 points, this can result in large cost savings. By installing automated fugitive emission sensing systems onto valves subject to the most demanding service conditions and thus most likely to develop leaks, compliance with the EPA regulations can be more readily achieved for the entire facility. This results in longer intervals between surveys for all of the valves, significantly reducing the time and expense of taking measurements manually from the valves without automated sensing systems.

Early detection of fugitive emissions from leaking valves also enables repairs to be made on a more timely basis, reducing the quantity of hazardous material emitted and reducing the cost of lost material. Accurate sensing of fugitive emissions provides an early warning system which can alert the facility operator to a potential valve seal failure and enable preventive measures to be taken before excessive leakage occurs.

However, employing an automated fugitive emission sensing system in an industrial environment requires designing a sample retrieval system which can efficiently collect fugitive emissions emanating from a piece of equipment and transport the emissions to gas sensors. The sample retrieval system must be capable of delivering a sample stream at a known flow rate in order to permit the gas sensors to make accurate and consistent measurements of the concentration of fugitive emissions. The sample retrieval system must be inexpensive to manufacture, and use a power source that is readily available in typical process plant, in order to keep installation costs to a minimum. The system must be suitable for use in hazardous areas subject to a risk of explosion, requiring electrical equipment to be of intrinsically safe or explosion-proof design. It also must be able to operate in harsh environments, including areas subject to hosing, high humidity, high and low temperatures, and vibration. The system also must be simple and reliable, in order to keep maintenance costs to a minimum.

Accordingly, it is an object of the present invention is to provide an apparatus and method for automatically collecting emissions from equipment that is suitable for industrial applications. Another object of the present invention is to provide an apparatus and method that provides for accurate and consistent collection of fugitive emissions. Another object of the present invention is to provide an apparatus to collect emissions can operate safely in hazardous environments. Another object of the present invention is to provide an apparatus and method to collect emissions that uses an existing pneumatic power source to collect the emissions. Yet another object of the present invention is to provide an apparatus that is simple and inexpensive to install. A further object of the present invention is to provide an apparatus and method to collect emissions that provides for low maintenance operation. A further object of the present invention is to provide an apparatus and method to collect emissions data and store the data for later retrieval. A further object of the present invention is to provide an apparatus and method to collect emissions data and communicate this data to a remote plant process control system. Yet a further object of the present invention is to provide an apparatus and method to collect emissions data and use this data to control the plant to reduce or eliminate the emissions. Yet a further object of the present invention is to provide an apparatus and method to collect emissions data and communicate this data to a remote plant process control system to enable control of the plant to reduce or eliminate the emissions.

SUMMARY OF THE INVENTION

In accordance with one aspect of the invention, there is provided an apparatus for collecting emissions from equipment where the apparatus includes a bonnet capsule enclosing at least a portion of the equipment. The apparatus also includes an ejector in fluid flow communication with the bonnet capsule. A source of pressurized fluid, which may be the plant instrument air supply, is connected to the ejector, such that the flow of pressurized fluid through the ejector creates a pressure drop which draws any emissions from the bonnet capsule into the ejector.

In accordance with another aspect of the invention, there is provided an apparatus for collecting emissions from equipment and storing the data for later retrieval. The data may be used to control plant conditions to reduce or eliminate the emissions. The data may also be communicated to a separate process control system, which may control plant conditions to reduce or eliminate the emissions.

In accordance with another aspect of the invention, there is provided a method for collecting emissions from equipment comprising enclosing at least a portion of the equipment with an enclosure, connecting an ejector in fluid flow communication with the enclosure; and supplying pressurized fluid to the ejector, thereby creating a pressure drop in the ejector which acts to draw the emissions from the equipment into the ejector.

BRIEF DESCRIPTION OF THE DRAWINGS

The features and advantages of the present invention will be best appreciated upon reference to the following detailed description and the accompanying drawings, in which.

Figure 1:
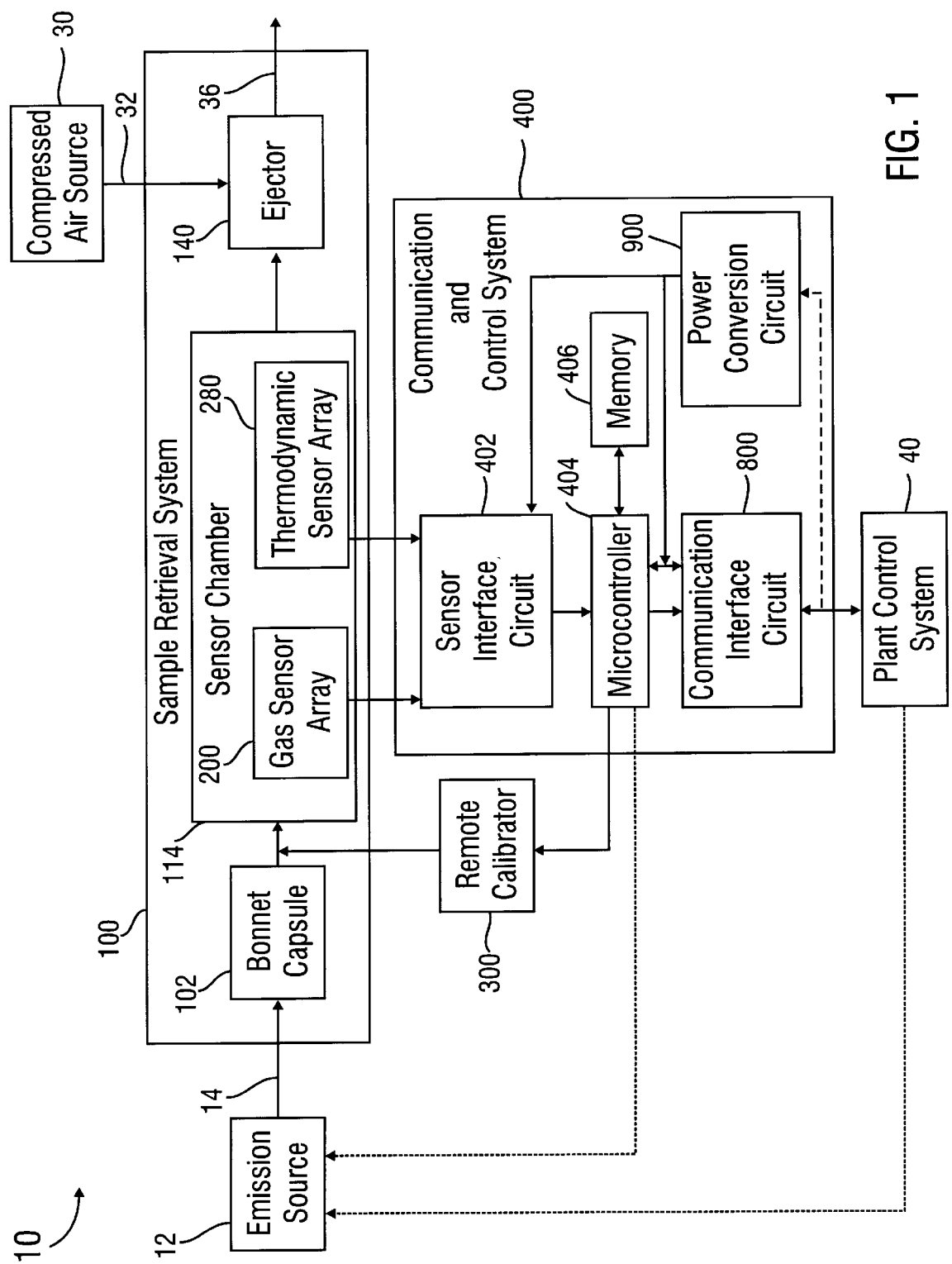
FIG. 1 is a block diagram of an illustrative embodiment of the invention showing the major components of a sample retrieval system integrated into a fugitive emission sensing system.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DESCRIPTION OF ILLUSTRATIVE EMBODIMENTS

Turning now to the drawings and referring initially to FIG. 1, a block diagram of an illustrative embodiment of the invention is given showing the major components of a sample retrieval system 100 integrated into a fugitive emission sensing system 10. An emission source 12 is shown, from which a sample stream 14 is drawn into sample retrieval system 100. The sample stream 14 includes any emissions (also referred to as the analyte) emanating from emission source 12. The sample retrieval system 100 includes bonnet capsule 102, sensor chamber 114, and ejector 140. A gas sensor array 200 and thermodynamic sensor array 280 are located within the sensor chamber 114. The sample stream 14 is drawn from the bonnet capsule 102 into the sensor chamber 114, exposing the gas sensor array 200 and the thermodynamic sensor array 280 to the sample stream 14. The sample stream 14 then passes into the ejector 140. A compressed air source 30 provides compressed air 32 to the ejector 140, creating a pressure drop within the ejector 140 which draws the sample stream 14 through and sensor chamber 114 and into the ejector 140. The compressed air 32 and sample stream 14 are mixed within the ejector 140 and exhausted to atmosphere as the mixture 36. The sample retrieval system 100 is integrated with a remote calibration system 300, which is arranged to inject a small quantity of the analyte being measured into the sample stream to enable automated calibration of the gas sensors.

In addition, control and communication system 400 is provided to process the sensor outputs and perform control and communication functions for the fugitive emission sensing system 10. The control and communication system 400 includes sensor interface circuit 402, microcontroller 404, memory 406, communication interface circuit 800, and power conversion circuit 900.

The gas sensor array 200 and thermodynamic sensor array 280 are connected to sensor interface circuit 402, which processes the signals from the sensor arrays and provides the processed signals to microcontroller 404. A suitable gas sensor and sensor interface circuit is described in U.S. application Ser. No. 08/968,081, (attorney's docket number FEMR:013) by John P. Dilger and Nile K. Dielschneider, entitled High Frequency Measuring Circuit, filed concurrently herewith, the disclosure of which is hereby incorporated by reference. The microcontroller 404 stores the data from the sensors in memory 406, and may use the sensor data received from the fugitive emission sensing system 10 to initiate control actions to reduce or eliminate the emissions. For example, the microcontroller 404 could close a valve upstream from the emissions source 12 to stop the flow of fluid through the emissions source 12 in order to stop emissions caused by leakage of the fluid. Alternatively, the microcontroller 404 could alter the operating condition of the emissions source 12 itself to reduce or eliminate the fugitive emissions. Microcontroller 404 may use communication interface circuit 800 to provide these control signals to the upstream valve, the emissions source 12, or any other plant equipment that may be used to reduce or eliminate the emissions.

Microcontroller 404 may also use communication interface circuit 800 to provide sensor data to a process control system 40. The fugitive emission sensing system 10 may perform measurements of fugitive emissions and immediately communicate the resulting sensor data to a separate process control system 40. Alternatively, the fugitive emission sensing system 10 may store sensor data from each measurement for later retrieval by the process control system 40.

The communication interface circuit 800 also may receive data and control commands from the process control system 40. The process control system 40 may use the sensor data received from the fugitive emission sensing system 10 to initiate control actions to reduce or eliminate the emissions. For example, the process control system 40 could close a valve upstream or alter the operating condition of the emissions source 12 as described above to reduce or eliminate the fugitive emissions.

The power conversion circuit 900 receives electrical power, which may be transmitted over the communication link with the process control system 40, and provides power to the communication and control system 400 at a suitable voltage.

The fugitive emission sensing system 10 may be used to detect the presence or measure the concentration of various types of fluids emitted from the emission source 12. The system may be used to detect hazardous, toxic, or polluting substances emitted from the source, or to detect leakage of non-hazardous substances the loss of which may be a cause of concern. The fugitive emission sensing system may be used to detect emissions from any kind of source, particularly industrial process equipment from which hazardous substances may leak. Examples include control valves, block valves, or pumps installed on lines carrying hazardous gases; agitators, screw conveyors, or other equipment installed on process vessels containing hazardous fluids; and heat exchangers, reactors, and other process vessels containing hazardous fluids. When emissions are detected by the fugitive emission sensing system 10, this data may be used by the fugitive emission sensing system 10 to control the process in such a way as to reduce or eliminate the emissions. Alternatively, the data may be transmitted to a remote plant process control system 40 which may respond by controlling the process in such a way as to reduce or eliminate the emissions.

Figure 2:
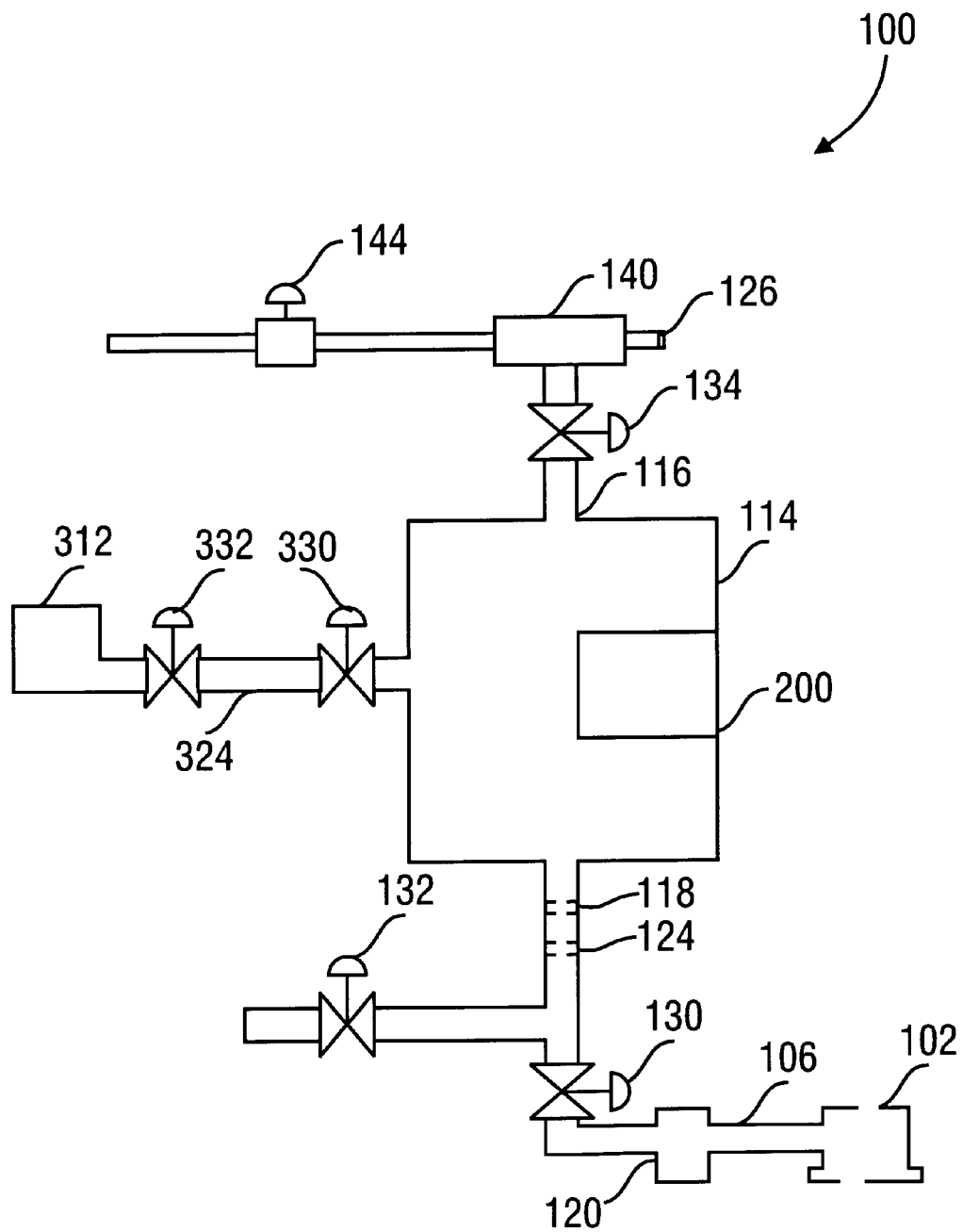
FIG. 2 is a diagram of a sample retrieval system according to the present invention.

Turning now to FIG. 2, a diagram is shown of the sample retrieval system 100 for use in the fugitive emission sensing system of FIG. 1. The sample retrieval system 100 comprises a bonnet capsule 102, retrieval manifold 106, sensor chamber 114, and ejector 140. The bonnet capsule 102 is comprised of an enclosure designed to enclose the surface area of the emission source 12 from which an emission is anticipated. The manifold 106 is connected at one end to the bonnet capsule 102 and at the other end to the sensor chamber 114, and permits a sample stream to flow from the emission source into the sensor chamber 114. The manifold 106 is preferably constructed of 316 stainless steel tubing or other suitable corrosion resistant material.

The sensor chamber 114 contains the gas sensor array 200, and may also contain a thermodynamic sensor array (not shown). The outlet 116 of the sensor chamber 114 is the inlet to the ejector 140. A pneumatic restriction is provided by a restriction orifice 118 at the inlet to the sensor chamber 114. The restriction orifice 118 induces a pressure drop in the sensor chamber to assist in the operation of the ejector 140. The restriction orifice 118 may be constructed from sapphire, stainless steel, or other suitable material which is inert to the emissions expected from the equipment being monitored.

A particulate filter 120 is located along retrieval manifold 106 to collect any particles entrained in the sample stream. Flame path restrictors 124 and 126 are provided at the inlet to the sensor chamber 114 and outlet from ejector 140. Microvalves 130, 132, and 134 are located at various positions to provide for isolation of various parts of the sample retrieval system. Microvalve 130 may be used to isolate the bonnet capsule 102 from the sensor chamber 114. Microvalve 132 provides the ability to draw ambient air into the sensor chamber 114, permitting a base line calibration to be performed on the gas sensors by closing microvalve 130 and opening microvalves 132 and 134.

A remote calibrator 300 may be connected to the sample retrieval system to enable the gas sensors to be calibrated without removing them from the sensor chamber 114. The remote calibrator analyte cell containing calibrant is connected through a first microvalve to a dosing chamber. The dosing chamber 308 is connected through a second microvalve to sensor chamber 114.

The sensor chamber 114 is preferably constructed of cast aluminum. The interior of the chamber may be left unfinished, or coated or machined to achieve a smooth finish to reduce surface sorption of gases from the sample stream. The sensor chamber 114 may be constructed of other suitable corrosion resistant materials that are not affected by the emissions being monitored. The sensor chamber 114 is preferably constructed as a modular unit to permit replacement of the unit in the field.

Figure 3:
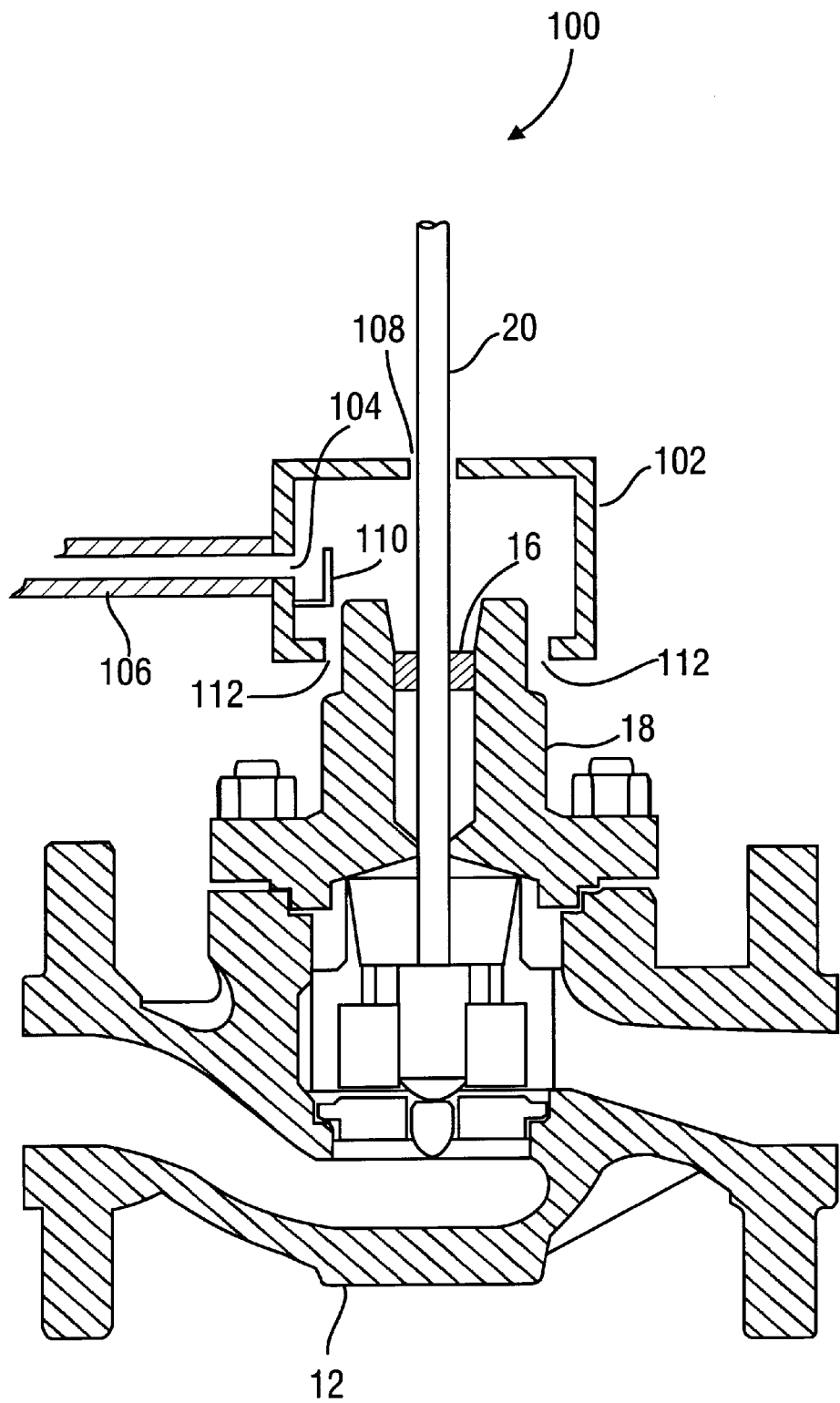
FIG. 3 is a sectional view showing details of the bonnet capsule of the sample retrieval system of FIG. 2.

Turning now to FIG. 3, a sectional view is shown of the bonnet capsule of the sample retrieval system 100 of FIG. 2. The bonnet capsule 102 is shown mounted on an emission source 12, depicted in the drawing as a control valve. The bonnet capsule 102 includes an outlet 104 to which the retrieval manifold 106 is connected, and may also include an opening 108 to permit installation of the bonnet capsule 102 around a valve stem 20 or other obstructing parts of the emission source. The arrangement of the bonnet capsule 102 shown in FIG. 2 is designed to collect gas leaking from the valve stem packing 16 located between the valve body 18 and valve stem 20. The opening 108 is designed to have a small clearance between the valve stem and the bonnet capsule wall to limit the entry of foreign particles into the bonnet capsule 102. A baffle 110 is positioned inside the bonnet capsule 102 to restrict foreign particles in the bonnet capsule 102 from entering the retrieval manifold 106.

The bonnet capsule 102 is mounted on the emission source so that a gap 112 remains between the bonnet capsule 102 and the emission source 12. This creates a low impedance pneumatic restriction, which permits air to flow through gap 112, through the bonnet capsule 102, and into retrieval manifold 106. This air flow carries any fugitive emissions emitted from the emission source into the retrieval manifold 106 and on into the sensing chamber. This continual airflow also prevents fugitive emissions from emission source 12 from accumulating in the bonnet capsule. Such an accumulation can result in a false high sensor reading due to the integration effect of an accumulation of fugitive emissions.

The bonnet capsule may be constructed of two or more pieces to facilitate installation in situations where the bonnet capsule 102 must be installed around obstructing members. Thus, a bonnet capsule 102 as shown in FIG. 3, comprising an enclosure split vertically into two halves, may be installed around the valve stem 20 without removing a valve actuator mounted at the top of the valve stem (not shown). The bonnet capsule 102 is preferably constructed on 316 stainless steel or other suitable corrosion resistant material.

Figure 4:
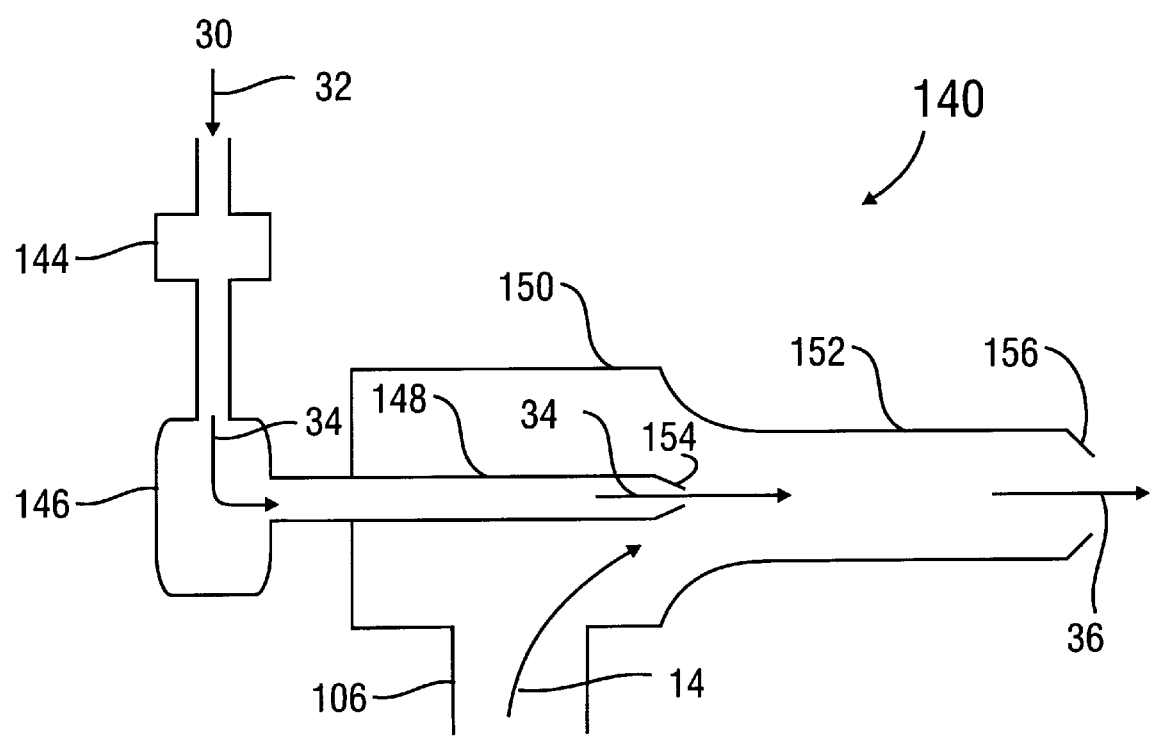
FIG. 4 is a sectional view showing details of the ejector of the sample retrieval system of FIG. 2.

FIG. 4 is a sectional view showing details of the ejector 140 of the sample retrieval system 100 of FIG. 2. The ejector 140 may be integral to the sensor chamber 114 or may be constructed as a separate unit. A compressed air source 30 provides compressed air 32 to a microregulator 144 which provides regulated compressed air 34 to the ejector 140. The compressed air is used to provide the motive power to draw the sample stream 14 from the bonnet capsule 102, through the sensor chamber 114, and into the ejector 140. The compressed air source 30 may be the instrument air supply typically used in process plants to modulate pneumatic control valves or operate pneumatic instruments, although other sources of pressurized gas or liquid may be used. The microregulator 144 is a small pressure regulator of a type commonly used in industrial applications. The microregulator 144 reduces and regulates the pressure of the compressed air to control the flow of the sample stream 14 and minimize the consumption of compressed air 32.

A primary chamber 146 receives regulated compressed air 34 from the microregulator 144 and discharges air into a primary nozzle 148. The primary nozzle 148 is tubular in shape, with an orifice 154 discharging into the throat of the secondary nozzle 152. A secondary chamber 150 is connected to manifold 106 and to the throat of secondary nozzle 152. The secondary nozzle 152 is tubular in shape, with a larger cross-sectional area than the primary nozzle 148, and an orifice 156 discharges to atmosphere.

In operation, the regulated compressed air 34 enters the primary chamber 146 and flows into the primary nozzle 148. The regulated compressed air 34 increases in velocity as it enters the constricted region at the outlet of the primary nozzle 148. This high velocity stream of compressed air discharges into the secondary nozzle 152, entraining air from the secondary chamber 150 and creating a pressure drop in the secondary chamber 150. This pressure drop induces the flow of sample stream 14 from the bonnet capsule 102, through the retrieval manifold 106, and into the secondary chamber 150. Sample stream 14 carries any fugitive emissions from the emission source 12 through the sample retrieval system, exposing the gas sensor array 200 and thermodynamic sensor array 280 to the emissions. The regulated compressed air 34 and the sample stream 14 are mixed together in the secondary nozzle 152 and the mixture 36 is exhausted to atmosphere.

The ejector 140 may be made of stainless steel, or other corrosion resistant material. The primary orifice 154 and secondary orifice 156 are preferably constructed of sapphire.

The ejector 140 is designed to produce a sample stream 14 of known mass flow through the sample retrieval system 100. The flowrate of the sample stream 14 is determined by the diameters of the primary orifice 154, secondary orifice 156, sensor chamber inlet orifice 118, and the pressure of regulated compressed air 34. The sample retrieval system 100 operates satisfactorily at a sample stream flowrate of about 0.425 square cubic feet per hour. This flowrate may be achieved with a primary orifice diameter of 0.011 inches, secondary orifice diameter of 0.024 inches, sensor chamber inlet orifice diameter of 0.013 inches, and regulated compressed air pressure of about 3.0 pounds per square inch gauge. However, different dimensions and operating conditions for the ejector 140 may be required to effectively collect emissions from different types of emissions sources.

By controlling the pressure of the regulated compressed air 34 into the ejector 140, the pressure drop within the secondary chamber 150 can be controlled, and thus the velocity of the sample stream 14 through the retrieval manifold 106 and sensor chamber 114 can be controlled. Furthermore, the mass flow of the sample stream 14 can be calculated given the geometry of the ejector 140, retrieval manifold 106 and sensor chamber 114, and the pressure of the compressed air at the inlet to the primary chamber 146.

The design of the sample retrieval system 100 thus eliminates the need for a mass flow sensor to measure the sample stream flow through the retrieval manifold 106. The system described also eliminates the need for pumps or fans located near the emission source to collect the sample stream, resulting in a simple and inexpensive design. Lastly, the sample retrieval system can be designed to conform to EPA sample collection requirements.

Many modifications and variations may be made in the techniques and structures described and illustrated herein without departing from the spirit and scope of the present invention. Accordingly, it should be understood that the methods and apparatus described herein are illustrative only and are not limiting upon the scope of the present invention.

What is claimed is:

1. A system for collecting emission samples from a control valve having a valve stem, the system comprising:

a capsule defining an opening to permit installing the capsule around the valve stem, the capsule including an outlet;

a sensor chamber having an inlet and an outlet;

a fluid passage coupling the inlet of the sensor chamber to the outlet of the capsule;

an ejector coupled to the outlet of the sensor chamber and connectable to a source of pressurized fluid, such that pressurized fluid flowing through the ejector creates a pressure drop to induce the flow of a sample stream from the capsule, through the sensor chamber, and into the ejector, the sample stream mixing with the pressurized fluid in the ejector and being exhausted therefrom; and a baffle situated within the capsule to restrict foreign particles from entering the fluid passage.

2. The system of claim 1 wherein said capsule comprises a plurality of pieces adapted to encircle at least a portion of said valve stem.

3. The system of claim 1 wherein said pressurized fluid comprises compressed air.

4. A system for collecting emission samples from a control valve having a valve stem, the system comprising:

a capsule including an outlet, the capsule comprising an enclosure split vertically into two halves and defining an opening to allow installing the capsule around the valve stem;

a sensor chamber having an inlet and an outlet;

a fluid passage coupling the inlet of the sensor chamber to the outlet of the capsule; and an ejector coupled to the outlet of the sensor chamber and connectable to a source of pressurized fluid, such that pressurized fluid flowing through the ejector creates a pressure drop to induce the flow of a sample stream from the capsule, through the sensor chamber, and into the ejector, the sample stream mixing with the pressurized fluid in the ejector and being exhausted therefrom.

5. The system of claim 4 wherein said capsule is adapted to form a low impedance restriction against said control valve.

6. The system of claim 4 wherein said control valve includes valve stem packing having an exterior surface and wherein said capsule circumferentially encloses said exterior surface of said valve stem packing of said valve.

7. The system of claim 4, further comprising:

a communication and control system connected to said sensor for generating data indicative of the concentration of said emissions drawn from said control valve.

8. The system of claim 7 further comprising a process control system remotely connected to said communication and control system for receiving said data to control said central valve to reduce said emissions.

9. The system of claim 8 wherein said communication and control system comprises means for storing data indicative of concentration of said emissions from said central valve.

10. The system of claim 7 wherein said communication and control system comprises means for using said data to control said central valve to reduce said emissions.

11. The system of claim 4 wherein said ejector comprises a primary nozzle and a secondary nozzle, said primary nozzle adapted to receive said pressurized fluid and discharge said pressurized fluid into said secondary nozzle.

12. The system of claim 11 further comprising a microregulator to regulate the pressure of said pressurized fluid before said primary nozzle receives said pressurized fluid.

13. The system of claim 4 wherein said sensor chamber is integral with said ejector.

14. The system of claim 4 further comprising a source of calibration fluid in fluid flow communication with said sensor chamber.

15. The system of claim 4 wherein said pressurized fluid comprises compressed air.

16. The system of claim 4, wherein the ejector induces a sample stream having a known mass flow rate.

* * * * *